United States Patent [19]

Shehad

[11] Patent Number: 5,324,857

[45] Date of Patent: Jun. 28, 1994

[54] INHIBITION OF THE FORMATION OF NITROSAMINES

[75] Inventor: Noel S. Shehad, Taylor Lake Village, Tex.

[73] Assignee: Solvay Interox, Houston, Tex.

[21] Appl. No.: 874,710

[22] Filed: Apr. 28, 1992

[51] Int. Cl.$^5$ ............ C07C 291/04; C07C 243/06
[52] U.S. Cl. .................. 564/298; 564/2; 564/15; 564/76; 564/102; 564/112; 564/113; 564/300; 564/301; 562/471; 560/61; 560/67; 546/184; 594/173; 540/474
[58] Field of Search ............ 564/2, 298, 55, 76, 564/102, 300, 301, 112, 113; 540/474; 544/173; 546/184; 568/701, 716, 717; 560/61, 67; 562/471

[56] References Cited

U.S. PATENT DOCUMENTS

| | | | |
|---|---|---|---|
| 2,169,976 | 8/1939 | Guenther et al. | 260/521 |
| 2,419,283 | 4/1947 | Paul et al. | 260/306.6 |
| 2,795,611 | 6/1957 | List | 260/563 |
| 3,122,417 | 2/1964 | Blaser et al. | 423/272 |
| 3,234,140 | 2/1966 | Irani | 252/186 |
| 4,144,272 | 3/1979 | Bergomi et al. | 260/567 |
| 4,247,480 | 1/1981 | Murata et al. | 564/298 |
| 4,304,762 | 12/1981 | Leigh | 423/272 |
| 4,970,341 | 11/1990 | Summerford | 564/298 |
| 5,023,376 | 6/1991 | Shehad et al. | 564/298 |

FOREIGN PATENT DOCUMENTS

| | | | |
|---|---|---|---|
| 307184 | 3/1989 | European Pat. Off. | 564/298 |
| 320694 | 6/1989 | European Pat. Off. | 564/298 |
| 83465 | 7/1981 | Japan | 564/298 |
| 7401261 | 8/1974 | Netherlands . | |

*Primary Examiner*—Shailendra Kumar
*Attorney, Agent, or Firm*—Larson and Taylor

[57] ABSTRACT

Reaction of amine-containing substrates with hydrogen peroxide can suffer from certain problems, especially in the presence of transition metals. These problems include both in situ generation of impurities and particularly nitrosamines, which are allegedly carcinogenic, and also impaired product formation, The problems can be ameliorated by employing in the reaction mixture free radical scavengers, including in particular phenols and polyhydroxy-substituted aromatic compounds. The scavengers are advantageously employed in conjunction with a metal chelating agent such as polycarboxylic acid or an organopolyphosphonic acid.

11 Claims, No Drawings

INHIBITION OF THE FORMATION OF NITROSAMINES

The present invention relates to a process for the inhibition of the formation of nitrosamines during the reaction of a compound containing an amine functionality, and in particular from secondary or tertiary amines.

BACKGROUND TO THE PRESENT INVENTION

Compounds containing an amino functionality can be oxidized with hydrogen peroxide, sometimes with an additive such as a catalyst in order to promote the reaction or sometimes in the absence of a catalyst, depending on the inherent reactivity of the substrate. Many papers or patents describe variations to the reaction between amines and hydrogen peroxide. For example, U.S. Pat. No. 4 247 480 to Nissan Chem Ind KK suggests the addition of a chelating agent selected from EDTA or stannate together with carbonic acid or a carbonate.

Disadvantageously, however, there is a tendency for nitrosamines to be formed as byproducts in reaction mixtures which contain amines, particularly secondary or tertiary amines and hydrogen peroxide. This is inevitably the case during reaction between those two reactants but it can also occur if such an amine is itself a reaction product or intermediate. For example, when tertiary amines are being converted to amine oxides by reaction with hydrogen peroxide, there is a distinct tendency for nitrosamines to be produced as a byproduct. The formation of nitrosamines is disadvantageous for several reasons, of which the most significant identified to date is the fact that many nitrosamines are carcinogenic. At least some of the nitrosamines are quite volatile, so that either in the course of the reaction or subsequently during storage or use of the main product, such volatile nitrosamines can be released into the atmosphere and thus can be inhaled by persons in the vicinity. They can be absorbed through the skin by dermal contact. This can be particularly significant for some amino derivatives such as amine oxides, in that one of their major uses is in personal hygiene products, such as shampoos or cleansing lotions which are skin contact products. Consequently, it is highly desirable to find ways of inhibiting the formation of such carcinogenic byproducts to preserve the health of chemical process operators and any subsequent user of the products.

As a second disadvantage, though of rather less importance, a number of the byproduct nitrosamines are brightly colored, such that their presence, even in low amounts, tends to impart that color to the main product. If as is the case with amine oxides, the product would otherwise be white, then the presence of the byproduct can render the product less desirable commercially, by failing to meet color specifications.

It has been observed that the peroxide/amine reaction can be sensitive to the presence of a number of interfering substances including metals which can promote by-reactions. Such substances can be present as impurities in the reactants, possibly as a result of the method of their manufacture, or introduced in water added as diluent in the reaction mixture, or can be extracted from the pipework or walls of the reaction vessels or holding tanks or can result from inadvertent ingress of foreign bodies such as dust. The concentration of such substances correlates to a reasonable extent with the extent of nitrosamine formation. Herein, when high levels of such interfering substances are present, though still within the range that can be encountered in practice, the conditions are sometimes described as "stress conditions".

In U.S. Pat. No. 5 023 376 (Shehad et al) and the corresponding EP-A-0 409 043 (Interox America), it has already been proposed to conduct amine/hydrogen peroxide reactions in the presence of a specified selection of aminopolymethylenephosphonate compounds. Together with other beneficial effects, it was found that their addition, in appropriate concentrations, resulted in the measurable reduction in the rate and/or extent of formation of nitrosamines. It can therefore be deduced from the data disclosed therein that at least some transition metal ions are in some way implicated in the mechanism for nitrosamine formation. The problem was ameliorated by chelation with the selected phosphonates, but either to a lesser extent or not appreciably by employing other organophosphonates outside the selection. From the foregoing, it was deduced that some further mechanism may be operating to generate nitrosamines or that there was some hitherto unidentified factor within the existing metal ion catalyzed route for nitrosamine formation that was contributing to the byproduct formation.

OBJECT OF THE PRESENT INVENTION

It is an object of the present invention to find alternative or additional means to inhibit the formation of nitrosamines in reaction mixtures containing amines and hydrogen peroxide.

BRIEF SUMMARY OF THE INVENTION

According to the present invention there is provided a process for the inhibition of nitrosamine formation in a reaction mixture containing hydrogen peroxide and a secondary or tertiary amine which is characterized by incorporating in the mixture an effective amount of a free radical scavenger.

According to a related aspect of the present invention, there are provided reaction mixtures containing a reactive concentration of a secondary or tertiary amine and of hydrogen peroxide in which is incorporated a free radical scavenger in a concentration that is effective to inhibit nitrosamine formation.

Herein, the term "effective" with regard to free radical concentration or amount means such an amount or concentration which causes a detectable reduction in measurable total nitrosamine concentration in the reaction mixture. The term "inhibit" indicates at least a partial suppression of the rate or extent of nitrosamine formation.

DETAILED DESCRIPTION OF THE INVENTION

Free radical scavengers are well known in the field of organic synthesis and many commercial products are sold specifically for that function. In general, the scavengers are selected from amongst phenols or polyols or thiols. Though not exclusively, it is generally desirable to select scavengers having a recognized capability to scavenge hydroxyl radicals.

Phenol itself may be used. Many particularly suitable scavengers are selected from phenols which satisfy the general formula i):-

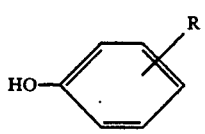

in which R represents at least one substituent selected from alkyl, ether, hydroxyl, carboxylic acid and aliphatic carboxylic acid ester groups. Normally R in formula i) represents from 1 to 4 substituents.

The effectiveness in scavenging of phenolic compounds is presently believed to derive at least in part from the proximity of the benzene nucleus to the hydroxyl group, and thereby take advantage of charge delocalization following interaction of a free radical with the scavenger. Nonetheless, the present invention is not predicated upon any theory, belief or explanation given herein as to how or why the chosen materials described herein function, but instead on the results obtained.

In some phenolic scavengers according to formula i), R represents a plurality of alkyl substituents, particularly low weight groups from methyl to butyl, and especially substituents ortho and/or para to the hydroxyl group. Preferably all three ortho and para positions are alkyl substituted in such scavengers, such as in 2,6-di-t-butyl-4-methylphenol.

In a number of particularly suitable scavengers for use in the present invention, R represents in formula i) one or two hydroxyl substituents, and optionally at least one further non-hydroxyl substituent.

In scavengers according to formula i) in which R represents a plurality of substituents, each substituent may be the same or different. In several instances, R represents an alkyl, carboxylic acid/ester or ether substituent in addition to representing at least one hydroxyl group.

One suitable sub-class of phenolic scavengers comprises polyhydroxybenzoic acid or alkyl ester derivatives thereof, the benzene nucleus optionally being further substituted by one or more alkyl substituents. Normally not more than a single carboxylic acid/ester substituent is present. Included within that sub-class are the dihydroxybenzoic acids, gallic acid, pyrogallic acid and ester derivatives thereof. Other suitable sub-classes comprise polyhydroxyalkylbenzenes or ether derivatives thereof. Representatives of that subgroup include alkylresorcinols and alkylhydroquinones.

Where R comprises or includes an alkyl group, either as a substituent in its own right or as part of an ester or ether substituent, said alkyl moiety may conveniently contain up to 6 carbons which can be linear or branched for propyl to hexyl, including tertiary groups for butyl to hexyl. Each of said alkyl groups, if a plurality is present, may be the same or different.

As a variation of the foregoing, some of the suitable phenol compounds comprise alkanes, such as a $C_3$ to $C_6$ alkane, often linear, which are substituted by a hydroxyphenyl substituent. In such scavengers, a plurality of hydroxyphenyl substituents such as up to 4 may be present. Such hydroxyphenyl substituents often obey formula ii):-

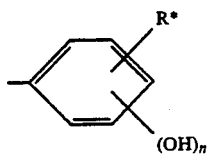

in which R* represents hydrogen or at least one alkyl group which may be selected from the same range of alkyl groups as for R in general formula i) and n represents an integer of from 1 to 3. In compounds obeying formula ii), R* can desirably represent two alkyl groups, such as one being a methyl and the other a butyl (particularly t-butyl). Desirably, the or one of the hydroxyl substituents is at the 4 position around the nucleus, as for example in a 2,5-dialkyl-4-hydroxyphenyl substituent.

The scavenger can also be selected from thiols or disulfides. Representative thiols embrace thiocarboxylic acids, including in particular low molecular weight compounds containing one or two aliphatic carboxylic acid substituents, each such substituent containing up to about eight carbons. Some preferred compounds comprise thiodialiphatic carboxylic acids, such as thiodibutanoic acid. In such compounds the two aliphatic acids are often, though not exclusively, the same, as for example in thiodipropionic acid or thiodiacetic acid. Other thiols include aromatic or heterocyclic thiols, such as 2-benzimidazolethiol and related compounds. Disulfides include alkylthiuram disulfides and bis(dimethylthiocarbamoyl)-disulfide.

It will also be understood that a mixture of any two or more of the foregoing scavengers can be employed, including explicitly a mixture of examples from any two or more sub-classes of scavenger. Particular combinations comprise an alkylated hydroxyanisole with an alkyl gallate or an alkylcresol, including specifically 2-t-butyl-4-hydroxyanisole with either propyl gallate or 2,6-di-t-butyl-p-cresol.

Secondary or tertiary aliphatic alcohols have also been found in some instances to ameliorate the extent and/or rate of nitrosamines formation and it is convenient to employ such alcohols for example those containing at least 3 and particularly from 4 to 6 carbons. In one advantageous method of employment, such alcohols can act as solvent for phenolic scavengers, some of which are only poorly soluble in some reaction media, thereby enabling the latter to be more readily dispersed through the reaction medium or in at least one of the reactants, such as into the hydrogen peroxide.

The concentration of scavenger to employ in the reaction mixture in practice depends upon its inherent capability to scavenge and the anticipated level at which free radicals will be generated therein. The latter, in turn, is believed to depend, amongst other factors, on the extent of contamination and the nature of the contaminants, including a wide range of metal ions. A number of transition metal ions can induce free radical formation by interaction with hydrogen peroxide, i.e. with the co-reagent. Other free-radicals can arise from interaction of radiation with hydrogen peroxide or other constituents of the reaction mixture.

In practice, it is convenient to relate the amount of scavenger to add to the amount of amine in the reaction mixture. It is desirable to employ a mole ratio at least $10^{-5}$ mole of scavenger per mole of amine and in many instances a mole ratio of at least $10^{-4}:1$. The upper limit is at the discretion of the user and takes into account the expected maximum contaminant incursion. The mole ratio is normally not greater than $10^{-1}$ mole of scavenger per mole of amine and in many instances, the benefit is attained using scavenger:amine mole ratio of not more than about $10^{-2}$:1.

It will be understood that the scavenger may be introduced directly into the reaction mixture or at least a part of it may be introduced via one or both of the two reagents, namely the amine or the hydrogen peroxide solutions. Naturally, if it is introduced via either of the reagent solutions, the concentrations of scavenger therein are usually calculated so as to enable the total amount to fall within the above-identified limits in the reaction mixture. If desired, all the scavenger can be present when the amine and hydrogen peroxide reactants are mixed together, or a fraction, such as up to about half, of the scavenger may, if preferred, be introduced during the course of the reaction. In a number of reactions the hydrogen peroxide is employed in a small molar excess to the amine. In such circumstances, the desired concentration of scavenger can be obtained by dissolving it at approximately the same mole ratio relative to the hydrogen peroxide as would be desired relative to the amine. Naturally, the feasibility of supplying the entire amount of scavenger in the hydrogen peroxide solution is dependent upon the solubility of the former in the latter. In the case of aliphatic alcohols, this is readily achieved without any significant constraint, but for certain of the higher molecular weight aromatic compounds their solubility constrains the maximum that can be introduced this way. For such less soluble scavengers, it is preferable for at least a proportion of the total amount to be added either separately into the reaction mixture or into the amine reactant solution.

Preferably, the scavenger is employed in conjunction with a metal chelant such as a polyaminocarboxylic acid or organic polyphosphonic acid or a salt thereof. Many of the polyaminocarboxylic acids can be represented by the general formula

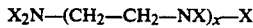
$X_2N-(CH_2-CH_2-NX)_x-X$ in which X represents $-CH_2CO_2H$ or a salt thereof and x an integer from 0 to 2, including EDTA and DTPA.

Organic phosphonates which can be employed together with the scavengers include hydroxyalkylenephosphonic acids, such as hydroxyethylene-1,1-diphosphonic acid and polyaminomethylene phosphonic acids. A number of such organic phosphonates are selected from alkylene aminomethylenephosphonic acids or water soluble salts thereof obeying either of the general formulae:-

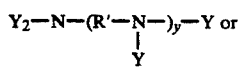
$Y_2-N-(R'-N-)_y-Y$ or (a)
          $|$
          $Y$

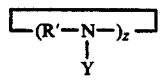
$\boxed{-(R'-N-)_z-}$ (b)
       $|$
       $Y$ in which Y represents a group of formula $-CH_2-PO_3M_2$ in which M represents H or a non-transition metal cation conferring water-solubility, R' represents an aliphatic diradical of 2 to 6 carbons, preferably 2 or 3 carbon atoms length or an alicyclic diradical containing from 2 to 6 carbon atoms, y represents an integer selected from 0 to 4, preferably from 1 to 4 and z represents an integer selected from 4 to 6. By the choice of particularly preferred metal chelates in conjuction with the scavenger, it is possible to combine the beneficial effects of the scavenger on inhibiting the formation of nitrosamines with the beneficial effect on inhibiting nitrosamine formation and improving product yield obtainable from the selected chelates. The two components complement each other.

Within the range of organic phosphonic acid compounds encompassed within formula 1 in the process of the instant invention, n is particularly suitably 1 or 2 and in compounds according to formula 2, m is preferably 4 or 6. For both formulae, adjacent amino groups are preferably separated by two linear carbon atoms which may bear simply hydrogen atoms or be substituted by a methyl group or form part of a 6 or 5 membered carbocyclic ring. It will be recognized that in such compounds, the length of the diradical is two carbon atoms. M can often represent a hydrogen atom or an alkali metal, ammonium or magnesium ion. Within formula 1, particularly preferred compounds include ethylenediaminetetrakis (methylenephosphonic acid), diethylenetriaminepentakis (methylenephosphonic acid) and 1,2-cyclohexanediaminetetrakis(methylenephosphonic acid) and the corresponding fully or partly neutralized sodium, potassium or ammonium salts thereof. Other suitable aminophosphonic acid compounds are the cyclic compounds within formula 2 which include tetracyclenetetrakis (methylenephosphonic acid) and hexacyclenehexakis (methylenephosphonic acid) and the corresponding fully or partly neutralized sodium, potassium or ammonium salts thereof.

Normally, the amount of chelate such as the selected phosphonic acid compounds is at least $10^{-5}$ moles per mole of amine and often from $5\times10^{-5}$ to $10^{-3}$ moles per mole amine.

One simple basis for selecting its amount comprises the total weight of the reaction mixture. The concentration of the chelate such as the preferred phosphonic acid compounds is preferably at least 15 ppm and desirably in the range of from 50 to 500 ppm, by which we mean parts by weight per million parts of the reaction mixture. It will be recognized that as concentrations rise from 15 to 50 ppm, the likelihood increases that the level of chelate and especially of preferred phosphonic acid compounds will be able to retain reaction efficiency for the desired reaction for an increasingly large proportion of transition metal contaminations and the combination of scavenger and chelate inhibit nitrosamine formation.

It will be recognized that the chelating compounds, e.g. phosphonic acid compounds can be introduced into the reaction mixture as a separate component thereof, or if more convenient, they can be incorporated together with one of the other components of the reaction mixture, such as preferably the aqueous hydrogen peroxide feedstock solution. It is especially desirable to employ concentrated hydrogen peroxide solutions which have been stored for at least a few days containing the aminophosphonic acid compounds. By so doing, it is believed that the resultant interaction between the aminophosphonic acid and the hydrogen peroxide induces a beneficial change to the phosphonic acid structure, possibly involving oxidation at the nitrogen atoms.

Naturally, the concentration of the phosphonic acid compounds in the hydrogen peroxide solution is selected in the light of the amount of hydrogen peroxide that it is intended to employ, and the concentration of hydrogen peroxide in the feedstock solution. Thus, to some extent, the concentration of the phosphonic acid compounds in the reaction mixture can vary depending upon the choice of amine being oxidized and its concentration in the peroxide solution can be prior adjusted to make due allowance for reagent useage to ensure that a suitable concentration of phosphonate is employed in the reaction mixture.

It will be recognized that the scavenger and chelate may be introduced together or separately into the reaction mixture. Thus, by way of example, in one embodiment, the chelate and scavenger are both premixed with the hydrogen peroxide solution, either as obtained from the supplier or in a dilution step. Alternatively, in other embodiments, all or part of the scavenger is introduced via the amine solution or directly into the reaction mixture and any chelate is introduced via the hydrogen peroxide solution.

The instant invention is particularly appropriate for use in the oxidation of substrates containing a secondary or tertiary amine group. Such reactions are often, though not exclusively conducted in aqueous conditions, ie water comprising the principal solvent, and some water is usually present either introduced with or arising in situ from the reaction of hydrogen peroxide. Particular reactions include the formation of amine oxides which obey:-

$$RR'R''N + H_2O_2 = RR'R''NO + H_2O \quad (1)$$

but can also be used in reactions for making hydroxylamines which may be expressed as:-

$$RR'NH + H_2O_2 = RR'NOH + H_2O \quad (2)$$

The invention is also appropriate for reactions involving a third reactant, which reactions naturally permit the two component interaction between amine and hydrogen peroxide. One particular example thereof comprises the production of sulfenamides, the reaction being:-

$$RSH + HNR'R'' + H_2O_2 = RS-NR'R'' + H_2O \quad (3)$$

Where the amine containing substrate also contains a further functionality which reacts in the presence of hydrogen peroxide, this too can result in nitrosamine formation as an undesirable by-product. One example comprises $$2RR'N-CS_2H + H_2O_2 = RR'N-CS_2-S_2C-NRR' + 2H_2O \quad (4)$$

The invention is applicable to any secondary or tertiary amine which can be oxidized using hydrogen peroxide. Thus, in particular it is applicable to amines in which the nitrogen substituents R, R' and R" each represent the same or different alkyl groups, each containing at least 1, often from 1 to 30 carbon atoms, and at least one of the groups can be a cycloalkyl group. The two groups R and R' can combine with each other and the nitrogen atom to form a heterocylic amine containing at least 4 carbon atoms, which optionally can itself be nuclearly substituted by an oxygen atom. One or more of the alkyl groups may have an aromatic substituent, e.g. dimethylaniline. The aliphatic amine substrate can also contain an ethoxylate or propoxylate chain, containing from 1 to 15 units. The aliphatic or heterocyclic amine substrate normally contains from 2 up to 50 carbon atoms. In many instances, the molecular weight of the amine substrate will fall within the range of from 80 to 325, and many of which contain from 6 to 22 carbon atoms.

Suitable low molecular weight amine substrates include dimethylamine and n- or isobutyldimethylamine, and the corresponding diethylamine compounds. Others include di and tributylamine, and cyclopentyldimethylamine.

In a number of desirable starting materials, at least one of the substituents R, R' and R" in the amine comprises a substituent containing at least 6 carbon atoms such as from 8 to 18 carbons. In some of such starting materials, only one substituent of R, R' and R" cantains at least 6 carbons and in other starting materials, two substituents each contain ate least 6 carbons. Such a substituent can comprise a long chain alkyl or cycloalkyl group. The long chain alkyl substituent may be linear, branched, or further substituted by or otherwise include within its structure a cycloalkyl group. Particular mention is made of linear C8 to C16 alkyl groups. The cycloalkyl substituent may be substituted by a short or long chain alkyl group. The remaining substituent or substituents of R, R' and R", are often short length alkyl groups containing from 1 to 5 carbon atoms, and in many instances are conveniently methyl or ethyl substituents. Thus, in one subset of suitable amines R and optionally R' is a linear C8 to C16 alkyl group or cyclohexyl and R' and R", if present and not already described, are methyl or ethyl. Examples of such alkylamines include hexyldimethylamine, 2-ethylhexyldimethylamine, octyldimethylamine, decyl-dimethylamine, dodecyldimethylamine, tetradecyl-dimethylamine, hexadecyldimethylamine and octadecyl-dimethylamine. Other examples include decylbutylethyl-amine, hexadecylhexylmethylamine, trioctylamine, cyclohexyldimethylamine, dicyclohexylmethylamine and cyclododecyldimethylamine.

Suitable heterocyclic amines include piperidine and morpholine and alkyl N-substituted derivatives thereof, and especially those in which R" is methyl or ethyl.

The invention process preferably employs at least a stoichiometric amount of hydrogen peroxide, which is often introduced in the form of a concentrated aqueous solution. In practical applications, it is often possible to employ under non-ideal reaction conditions, ie those in which significant contamination has occurred, a similar amount of peroxide to that which has hitherto been suggested in the art for reacting with the same substrate under "ideal" conditions. The benefit from employing free radical scavenger is manifested by inhibiting the extent of nitrosamine contamination particularly under contaminated conditions and together with the selected phosphonate compounds enabling a high substrate conversion to be maintained even under non-ideal conditions. In consequence, for example, the mole ratio of peroxide to aliphatic or heterocyclic tertiary amines in reaction (1) is normally not greater than 4:1, often less than 2:1 and in many practical instances is selected in the range of from 1.05:1 to 1.2:1. For reactions (2), (3) and (4), the amount of hydrogen peroxide to the secondary amine is normally less than ten times the stoichiometric amount and is preferably from about twice to four times the stoichiometric amount, ie the mole ratio is preferably from 2:1 to about 4:1 in reaction (2) or (3), and from 1:1 to 2:1 for reaction (4).

The invention process is normally carried out at a temperature of above ambient and often at up to about 80° C. All or most of the reactions can conveniently be effected at a temperature within the range of 40° to 75° C.

The reaction period is normally selected taking into account the reaction temperature and whether it is process (1), (2) or (3). In many instances, the period is chosen within the range of from 2 to 10 hours. The reaction period includes the period over which the hydrogen peroxide is normally introduced into the reaction mixture. This introduction period is often at least 20 minutes and normally not longer than about 100 minutes. In many instances it is from about 30 to about 60 minutes.

Having described the invention in general terms, specific embodiments thereof will hereinafter be described more fully by way of example thereof.

Comparison 1 and Examples 2 to 5

This Comparison and these Examples were each carried out using the following general method:-Dodecyldimethylamine (0.2012 moles, 42.94 g), and sufficient pure water to 150 g, ie approximately 106.9 g, were charged into a passivated 250 mL reaction flask, at ambient temperature together with 0.16 g of the stock metal solution described below to introduce 0.011 mmoles of transition metal impurities and thereby create stress conditions. A chelating agent, DTPA, viz diethylenetriaminepentacarboxylic acid, 0.043 mmoles, was then introduced into the mixture to provide a mole ratio to the metal of about 4:1.

The stock metal solution was obtained by dissolving $CuSO_4.5H_2O$, 0.393 g, $MnSO_4.H_2O$, 0.1475 g, $K_2CrO_4$, 0.0935 g, $Fe(NH_4)_2(SO_4)_2.6H_2O$, 3.5106 g, $AlK(SO_4)_2.12H_2O$, 8.791 g in 500 mL water (deionized) containing 20 mL of 10%w/w sulfuric acid solution. It contained a total of 2350 ppm metals concentration. Thus, the concentration of metals in the reaction mixture was about 2.3 ppm.

The reaction mixture was then heated to a temperature of 60° C. and stirred. An aqueous hydrogen peroxide solution, 50% w/w solution, stabilized by sodium pyrophosphate at 70 ppm calculated as $PO_4$, 15.03 g, was then delivered into the reaction mixture at a constant slow rate during the subsequent 45 minutes. In the Examples, but not in the Comparison, the hydrogen peroxide solution also contained 2.0 mmoles of a free radical scavenger, as specified below. When all the hydrogen peroxide had been introduced, the reaction temperature was increased to 75° C. and the reaction permitted to continue for a total of 4 hours. The mixture was then cooled and analyzed for yield of amine oxide and for the production of by-product volatile nitrosamines, specifically methyldodecylnitrosamine (MDNA) and nitrosodimethylamine (NDMA).

The free radical scavengers were respectively 2,6-di-tert-butyl-4-methylphenol (BHT) in Ex2, butylated hydroxyanisole, a mixture of 2-tert-butylmethoxy anisole and 3-tert-butylmethoxy anisole (BHA) in Ex3, ethyl gallate (EtG) in Ex4 and propyl gallate (PrG) in Ex5.

The results for the respective nitrosamine and total nitrosamine contents of the reaction mixture are given below.

|  | Scavenger | Nitrosamine content (ppb) | | |
|---|---|---|---|---|
|  |  | MDNA | NDMA | total |
| Comparison 1 | — | 2430 | 627 | 3057 |
| Example 2 | BHT | 1420 | 374 | 1794 |
| Example 3 | BHA | 652 | 127 | 779 |
| Example 4 | EtG | 334 | 73 | 407 |
| Example 5 | PrG | 230 | 78 | 308 |

From the foregoing, it can be seen that the addition of a free radical scavenger to a reaction mixture which already contained a carboxylate chelating agent resulted in a marked reduction in nitrosamine formation, and especially when ethyl gallate or propyl gallate was employed.

Comparison 6 and Examples 7 to 12

The procedure of Comparison 1 and Examples 2 to 5 was repeated, but substituting cyclohexane-1,2-diaminotetramethylenephosphonic acid (CDTMPA) for the DTPA, also in the same mole ratio of 4.3:1 to the metals, and in the Examples 2.0 mmoles of the following scavengers introduced into the reaction mixture:-BHT in Ex7, BHA in Ex8, EtG in Ex9, PrG in Ex10, thiodipropionic acid (TPA) in Ex11 and 2-butanol (BuL) in Ex12.

|  | Scavenger | Nitrosamine content (ppb) | | |
|---|---|---|---|---|
|  |  | MDNA | NDMA | total |
| Comparison 6 | — | 839 | 669 | 1508 |
| Example 7 | BHT | 212 | 123 | 335 |
| Example 8 | PHA | 151 | 125 | 276 |
| Example 9 | EtG | 57 | 30 | 87 |
| Example 10 | PrG | 59 | 21 | 80 |
| Example 11 | TPA | 444 | 97 | 541 |
| Example 12 | BuL | 582 | 679 | 1261 |

From the foregoing, it can be seen that the addition of a free radical scavenger to a reaction mixture which already contained a phosphonic acid chelating agent resulted in a marked reduction in nitrosamine formation, and especially when ethyl gallate or propyl gallate was employed. It can be seen that the combination of a phosphonic acid chelating agent and an hydroxybenzoic acid free radical scavenger was especially effective at inhibiting the formation of nitrosamine byproducts during the reaction.

What is claimed is:

1. A process for the inhibition of nitrosamine formation in a reaction mixture containing hydrogen peroxide and a secondary or tertiary amine which comprises incorporating in the mixture an effective amount of a free radical scavenger selected from the group consisting of phenols, aromatic polyols, thiols, and disulfides, and at least sufficient organic chelating agent to chelate transition metal impurities in the reaction mixture.

2. A process according to claim 1 in which the scavengers are selected from the group consisting of phenols, aromatic polyols, and thiols.

3. A process according to claim 1 in which the scavenger comprises a phenol which satisfies general formula i):-

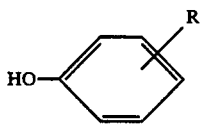

in which R represents at least one substituent selected from alkyl, ether, hydroxyl, carboxylic acid and carboxylic acid ester groups.

4. A process according to claim 3 in which R in formula i) for the scavenger represents from 1 to 4 substituents.

5. A process according to claim 3 in which R in formula i) represents at least one hydroxyl substituent and optionally at least one alkyl substituent.

6. A process according to claim 5 in which the scavenger is an acid compound selected form dihydroxybenzoic acids, gallic acid, and pyrogallic acid and from an ester or ether derivative of said acid compound.

7. A process according to claim 4 in which the scavenger comprises a C3 to C6 alkane substituted by up to 4 hydroxyphenyl substituents, which obey formula ii):-

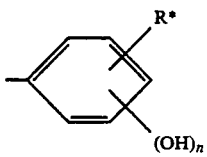

in which $R^*$ represents at least one alkyl group containing up to 6 carbons and n represents an integer of from 1 to 3.

8. A process according to claim 1 in which the scavenger is a thiodicarboxylic acid containing up to eight carbons.

9. A process according to claim 1 in which the scavenger is employed in molar ratio to the amine of from $10^{-5}:1$ to $10^{-1}:1$.

10. A process according to claim 1 in which the chelating agent is an aminopolycarboxylic acid or an organic polyphosphonic acid.

11. A process according to claim 10 in which the chelating agent is employed in a molar ratio to the amine of from $10^{-5}:1$ to $10^{-1}:1$.

* * * * *